United States Patent [19]

Fujiwa et al.

[11] Patent Number: 4,625,058

[45] Date of Patent: Nov. 25, 1986

[54] PREPARATION OF AN OXY-ACETYL COMPOUND

[75] Inventors: Takaaki Fujiwa; Hidetaka Kojima, both of Himeji, Japan

[73] Assignee: Daicel Chemical Industries, Ltd., Sakai, Japan

[21] Appl. No.: 710,821

[22] Filed: Mar. 12, 1985

[30] Foreign Application Priority Data

Mar. 23, 1984 [JP]  Japan .................................. 59-56542

[51] Int. Cl.$^4$ ...................... C07C 51/12; C07C 51/54
[52] U.S. Cl. .................................... 562/519; 260/546; 260/549
[58] Field of Search ................... 260/549, 544 A, 546; 560/232; 562/519

[56] References Cited

U.S. PATENT DOCUMENTS

| 4,252,741 | 2/1981 | Porcelli et al. ...................... 260/549 |
| 4,442,304 | 4/1984 | Erpenbach et al. ................ 560/232 |
| 4,497,967 | 2/1985 | Wan .................................... 260/549 |

*Primary Examiner*—Natalie Trousof
*Assistant Examiner*—L. Hendriksen
*Attorney, Agent, or Firm*—Flynn, Thiel, Boutell & Tanis

[57]            ABSTRACT

This invention provides a process for producing an oxy-acetyl compound by carbonylating an oxy-methyl compound with carbon monoxide in the presence of a rhodium catalyst, an iodine compound, and a metallic accelerator, and also in the presence of at least one compound selected from the group consisting of boron compounds, bismuth compounds, and tertiary amide compounds in the reaction system. When at least one of the bismuth or boron compound is present in the reaction system, the carbonylation reaction can proceed without precipitation of any metallic accelerator.

12 Claims, No Drawings

PREPARATION OF AN OXY-ACETYL COMPOUND

BACKGROUND OF THE INVENTION

1. Field of the Invention

This invention relates to a process for producing an O-acetyl compound such as acetic anhydride by reacting an O-methyl compound as a starting material, such as methyl acetate, with carbon monoxide by a catalytic reaction in which rhodium is used as a principal catalyst.

2. Description of the Prior Art

Acetic anhydride is used in quantity as a material for the production of cellulose acetate and, in addition, it is useful as a material for medicines, perfumes, dyes, etc.

Acetic anhydride has heretofore been produced industrially by a process in which ketene obtained by the thermal decomposition of acetic acid is reacted with acetic acid.

On the other hand, studies are being made actively to produce acetic anhydride by a reaction of carbon monoxide with methyl acetate or dimethyl ether. Although this reaction can proceed under a milder condition in a process in which rhodium is used as a principal catalyst than in processes in which other transition metal catalysts are used, it is not yet satisfactory in respect of its reaction rate in order to be used actually in the industry. Therefore, an improvement, in which a variety of reaction accelerators are incorporated in rhodium catalyst systems, has been made.

The additives for the rhodium-iodine compound (typical example being methyl iodide) catalyst system are typified by nonmetallic compounds, such as organo-phosphorus and organonitrogen compounds and, in addition, metallic accelerators are used in conjunction with, or separately from the nonmetallic compounds. A typical example of the metallic accelerator is chromium hexacarbonyl (Japanese Patent Laid-Open No. 115403/1976), and it is known from Japanese Patent Laid-Open Nos. 47922/1975, 52017/1975, etc., that chromium is effective. In addition, aluminum accelerators such as aluminum chloride and aluminum isopropoxide are also known (Japanese Patent Laid-Open Nos. 47922/1975 and 142234/1981). Further, zirconium (Japanese Patent Laid-Open No. 57733/1981) and titanium (Japanese Patent Laid-Open No. 142234/1981) are also known as metallic accelerators. It has been found that when an acetyl compound is produced by using these metallic accelerators, such as aluminum and chromium, the carboxylic acid salts of these metals sometimes form precipitates insoluble in the O-acetyl compound. This will bring about a considerable decrease in the concentration of a metallic accelerator in the reaction system and adversely affect the result of the carbonylation reaction. Further, a change in the composition due to precipitation is disadvantageous in repeating recirculation of a catalyst solution which is essential to the industrial production.

The solubility of an aluminum compound can be increased by proper selection of a solvent, for example, by using acetic acid as solvent, but in this case the aluminum compound is inevitably precipitated when the reaction solution is flash-distilled into a volatile component and a rhodium catalyst solution, though the decrease in the concentration in the reaction system can be prevented.

Japanese Patent Laid-Open Nos. 28980/1980, 57733/1981, etc. may be thought to be inventions in which the use of an insoluble metallic accelerator such as chromium is avoided.

SUMMARY OF THE INVENTION

As a result of a study on a technique for overcoming the above trouble of precipitation without avoiding the use of a useful metallic accelerator, the inventor of this invention has succeeded in solubilizing a metallic accelerator without detriment to a carbonylation reaction by adding a small amount of a certain compound.

Namely, an object of this invention is to provide a process for producing an O-acetyl compound by carbonylating an O-methyl compound with carbon monoxide in the presence of a rhodium catalyst, an iodine component, and a metallic accelerator, comprising carrying out the carbonylation reaction in the presence of at least one compound selected from the group consisting of boron compounds, bismuth compounds, and tertiary amide compounds in the reaction system. Examples of the metal species of the accelerators are those which easily form precipitates in the reaction system or the flash-distilled solution, for example, aluminum, chromium, and titanium.

DETAILED DESCRIPTION OF PREFERRED EMBODIMENTS

The carbonylation of an O-methyl compound according to the process of this invention is presumed to proceed through the carbonylation of methyl iodide present in the reaction system. Namely, this invention is applied to reaction processes including a carbonylation reaction of methyl iodide and a conversion of acetyl iodide and an O-methyl compound into a desired O-acetyl compound under a substantially anhydrous condition, for example, the production of acetic anhydride from methyl acetate and the production of acetic anhydride and acetic acid from a mixture of methyl acetate and methanol, whereupon the metallic compound in the reaction mixture or the concentrated flash-distilled solution can be solubilized, and an improvement in the rate of reaction or the conversion of an O-methyl compound can be realized. Further, this invention allows one to carry out repeated recirculation of a catalyst advantageously by preventing changes in the composition of a catalyst solution due to precipitation.

It may be presumed that the boron compound, bismuth compound or tertiary amide compound solubilizes a metallic compound accelerator in a reaction mixture or a concentrated solution by a chemical interaction. The amount of the compound used is not so large as that used when it serves as a solvent, and an amount which is equimolar to or smaller than that of an accelerator is sufficient for solubilization.

The inhibition of carbonylation by the addition of a boron compound is not recognized, but rather a higher rate of reaction can be obtained when a boron compound is added than when no boron compound is added. A bismuth compound or a tertiary amide compound does not inhibit a carbonylation reaction so long as it is used in a proper amount.

This invention will now be described in detail.

Rhodium which is used as a principal catalyst in this invention can be added to a reaction system as a compound exemplified as follows: an inorganic rhodium salt such as rhodium chloride, rhodium bromide, rhodium iodide or rhodium nitrate; a rhodium carboxylate such as rhodium acetate; rhodium acetylacetonate, a rhodium amine complex salt; an organorhodium complex such as trichlorotrispyridine rhodium, hydridocarbonyltris(triphenylphosphine)rhodium, chlorotris(triphenylphosphine)rhodium or chlorocarbonylbis(triphenylphosphine)rhodium; and a cluster complex such dodecacarbonyltetrarhodium. Although the amount of rhodium used is not necessarily limited strictly, it is used in a concentration of 0.1 to 50 mmol/l, preferably 10 to 30 mmol/l in terms of a concentration in a reaction solution.

In this reaction, a halide compound, especially an iodide compound, which is usually used in this field, is used, and the commonest typical example is methyl iodide. Although the amount of this compound is not necessarily limited, it is used in a concentration of 0.5 to 10 mol/l, preferably 1–5 mol/l in terms of a concentration in a reaction solution.

Examples of the aluminum compounds which are the typical accelerators applicable to this invention include aluminum salts of carboxylic acids such as formic, acetic, propionic, lauric, and stearic acid; aluminum alkoxides having a substituent group such as methoxy, ethoxy, or isopropoxy; aluminum halides having an element such as chlorine, bromine, or iodine, aluminum acetylacetonate, aluminum nitrate, and aluminum metal powder. Examples of the chromium compounds which are also typical metallic accelerators include metallic chromium, chromium hexacarbonyl and carboxylic acid chromium salts such as chromium acetate, and a chromium halide such as chromium iodide. The amount of the metallic accelerator used is one which provides an atomic ratio of a metal to rhodium of 0.1 to 100, preferable about 5 to 50. In order to obtain a sufficient effect, it is preferred that the concentration of a metallic accelerator in a reaction solution be above 0.1 mol/l, particularly 0.1 to 0.5 mol/l.

A boron compound which is one of the additives having a function of solubilizing a metallic accelerator in this invention can be used in an amount which provides an atomic ratio to the metal of the metallic accelerator of usually 0.1 to 15, preferably 0.4 to 2. Similarly, a bismuth compound is used in an amount which provides an atomic ratio of 0.05 to 2, preferably 0.1 to 1, and a tertiary amide compound is used in an amount to provide an atomic ratio of 0.5 to 10, preferably 1 to 2.

Examples of the boron compounds which can be used include metaboric acid, boron hydride $BH_3$, sodium borohydride, boric acid, borate esters, and boron acetate. When metaboric acid is used it reacts with acetic anhydride to form acetic acid and boron acetate (acetyl borate) in the first reaction, but the latter neither reacts with acetic anhydride nor inhibits the carbonylation reaction. When the reaction is carried out continuously by recycling a catalyst solution, no trouble arises from the recycled portion. It is of course possible to use a boron compound formed in the reaction system.

Examples of the bismuth compounds include bismuth nitrate and bismuth acetate, but other bismuth compounds, including those which are formed in the reaction system, may also be used.

Examples of the tertiary amide compounds include N-alkyllactams such as N-methylpyrrolidone and N-ethyl-pyrrolidone, and N,N-dialkylcarboxamide such as N,N-dimethylformamide, and N,N-dimethylacetamide.

The carbonylation reaction in this invention may be carried out in the presence of hydrogen, and this sometimes brings about a better result. The amount of hydrogen added is preferably in the range of concentration of 1 to 30%, based on a $H_2$/CO mixture. Although hydrogen can be used in a high concentration of 30% or above, by-products such as ethylidene diacetate and methane will increase in this case. Particularly, a concentration of hydrogen in the range of 5 to 20% is desirable from the viewpoint of a rate of carbonylation reaction and the formation of by-products.

In this invention, the reaction may be carried out in the presence of a carboxylic acid. Although acetic acid is the commonest one, aliphatic, alicyclic or aromatic carboxylic acids having 1 to 10 carbon atoms, such as propionic or butyric acid, can be used in some cases.

According to the process of this invention, a metallic accelerator can be solubilized in the reaction mixture or the catalyst solution even in the absence of a carboxylic acid as solvent which aids the dissolution of the metallic accelerator, so that it can be practiced without using any solvent such as acetic acid.

Although it is a common practice that a carboxylic acid such as acetic acid is added, as it is, to the reaction solution, it is also possible that a compound which can be converted into a carboxylic acid in the reaction mixture is added. In a typical example wherein the simultaneous production of acetic anhydride and acetic acid is carried out by carbonylating a raw material comprising a mixture of methyl acetate and methanol, it is not necessary that a compound is added in the form of a carboxylic acid. The amount of a carboxylic acid to be present in the reaction solution is usually 0.2 mol/l or above, preferably 1 mol/l or above, particularly preferably 2 mol/l or above. Although the amount of a carboxylic acid may be more than half the reaction mixture, it is usually within 80% of the reaction mixture because an unnecessarily large amount of a carboxylic acid causes a disadvantage of a lowered material concentration.

The starting materials to be carbonylated in this invention are those O-methyl compounds which form methyl iodide in the above reaction system, and the products are corresponding O-acetyl compounds. A typical example is the production of acetic anhydride by carbonylation of methyl acetate. Dimethyl ether can also be converted into acetic anhydride by carbonylation.

This invention is applicable to the production of acetic acid by carbonylation of methanol, but when only acetic acid is desired, the reaction can proceed at a sufficiently high rate of reaction without application of this invention by effecting the reaction in the presence of water in the reaction system. However, this invention is available also in the carbonylation of methanol, when a carbonylation product is obtained in the substantial absence of water as in the case where the simultaneous production of acetic anhydride and acetic acid is effected by carbonylating a raw material comprising mixture of methyl acetate and methanol.

Further, this invention is applicable to a carbonylation reaction of a carboxylic acid methyl ester, for example, formation of mixed anhydride of propionic and acetic acids (from which both propionic and acetic anhydrides can be formed by disproportionation) by carbonylation of methyl propionate.

The reaction temperature and the reaction pressure used in practicing this invention can be selected appropriately with reference to the prior art. The reaction temperature is usually 130° to 250° C., preferably 150° to 200° C., the pressure of carbon monoxide during the reaction is 1 to 100 kg/cm²G, preferably 5 to 100 kg/cm²G, especially preferably 20 to 80 kg/cm²G.

Examples set forth below for the purpose of illustrating the present invention include batchwise reactions performed in an autoclave, and flash distillation and batchwise hydrogen treatment suitable for the reaction, and the pressure is expressed in terms of feed pressure. However, it is of course possible that the process of the present invention can be carried out continuously by using techniques known to the art.

The amounts of remaining methyl acetate in the reaction mixture and of acetic anhydride formed were determined by means of gas chromatography. The conversion of methyl acetate was calculated according to the following equation:

$$\text{conversion (\%) of methyl acetate} = \frac{\text{amount of methyl acetate charged} - \text{amount of remaining methyl acetate in reaction mixture}}{\text{amount of methyl acetate charged}} \times 100$$

The rate of reaction was calculated on the basis of a pressure drop during the initial stage of a reaction. The yield of acetic anhydride was calculated according to the following equation:

$$\text{yield (\%) of acetic anhydride} = \frac{\text{amount of acetic anhydride formed (mol)}}{\text{amount of methyl acetate charged (mol)}} \times 100$$

EXAMPLE 1

A 300 cc Hastelloy B autoclave was charged with 1.29 mmol of rhodium chloride trihydrate (RhCl$_3$.3H$_2$O), 22 mmol of aluminum acetate, 22 mmol of metaboric acid, 4.9 ml of methyl iodide, 32 ml of methyl acetate, and 32 ml of acetic acid. After purging the atmosphere within the autoclave with carbon monoxide, the autoclave was pressurized with carbon monoxide to 40 kg/cm²G, and further pressurized with hydrogen (5 kg/cm²) to a total pressure of 45 kg/cm²G.

The reaction mixture was heated to 170° C. and reacted at this temperature for 1 hour. After the reaction, the mixture was cooled and released from the pressure, and the reaction mixture was discharged and a portion of this was analyzed by means of gas chromatography. Table 1 shows the results of the reaction. The reaction mixture was uniform and contained no solid precipitate. This mixture was transferred to a distillation apparatus and distilled at 100° to 130° C. until the volume of the reaction mixture was decreased to a half. The concentrated solution was checked about the presence of solid precipitate, but it was completely uniform and contained no solid precipitate.

The following examples were carried out in the same manner as in Example 1 except specified items and Table 1 shows the results of the reactions and the presence or absence of solid precipitate, with those of Examples 6 through 11 being shown in Table 2.

EXAMPLE 2 (Comparative)

No metaboric acid was added. A white solid precipitated from the concentrated solution gave an infrared absorption spectrum having an absorption assigned to aluminum acetate.

EXAMPLE 3

31.5 ml of acetic anhydride was used instead of acetic acid, and 11 mmol of metaboric acid was used.

EXAMPLE 4 (Comparative)

This example was carried out in the same manner as in Example 3, except that no metaboric acid was added. A white solid precipitated after the reaction gave an infrared spectrum having an absorption assigned to aluminum acetate.

EXAMPLE 5

20 ml of acetic anhydride was added instead of acetic acid. 238 mmol of metaboric acid was added. 434.8 mmol of acetic acid was formed by a reaction of acetic anhydride with metaboric acid.

TABLE 1

| Example | Rate of reaction (mol/l. hr) | Conversion of methyl acetate (%) | Yield of acetic anhydride (%) | Solid precipitate in reaction mixture | Solid precipitate in concentrated solution |
|---|---|---|---|---|---|
| 1 | 6.16 | 94.2 | 91.5 | nil | nil |
| 2 (comp.) | 7.3 | 80.1 | 74.6 | nil | white |
| 3 | 3.76 | 63.4 | 54.9 | nil | nil |
| 4 (comp.) | 2.95 | 58.4 | 53.0 | white | |
| 5 | 10.2 | 98.5 | 54.8 | nil | nil |
| 12 | 2.91 | 58.3 | 44.3 | nil | nil |
| 13 (comp.) | 1.04 | 29.0 | 19.8 | green | |
| 14 | 4.49 | 54.9 | 48.4 | nil | nil |
| 15 | 3.36 | 63.3 | 51.2 | nil | nil |
| 16 | 3.86 | 71.3 | 71.0 | nil | nil |
| 17 (comp.) | 5.12 | 82.0 | 79.5 | nil | white |
| 18 | 2.47 | 51.0 | 44.0 | nil | nil |
| 19 (comp.) | 2.40 | 45 | 40 | white | |
| 20 | 2.44 | 50.6 | 45.5 | nil | nil |
| 21 | 2.30 | 57.0 | 56.6 | nil | nil |
| 22 | 1.04 | 29.0 | 19.8 | green | |

EXAMPLES 6 through 11

(Odd-numbered examples are Comparative Examples)

These examples are those in which the ratio of acetic acid to acetic anhydride was varied. In all of the Comparative Examples in which no metaboric acid was used, a white solid was precipitated from the concentrated solution. Table 2 shows the conditions and the results.

EXAMPLE 12

11 mmol of chromium acetate was used instead of 22 mmol of aluminum acetate. 44 mmol of metaboric acid was used.

EXAMPLE 13 (Comparative)

This example was carried out in the same manner as in Example 12, except that no metaboric acid was added. After the reaction, a green solid was precipitated. This gave an infrared spectrum having an absorption assigned to chromium acetate.

EXAMPLE 14

2 mmol of bismuth nitrate was used instead of 22 mmol of metaboric acid.

EXAMPLE 15

11 mmol of boric acid was used instead of 22 mmol of metaboric acid. 32 ml of acetic anhydride was added instead of acetic acid.

EXAMPLE 16

A 405 cc autoclave was charged with 0.93 mmol of rhodium chloride trihydrate, 22 mmol of aluminum acetate, 22 mmol of N-methylpyrrolidone, 4.5 ml of methyl iodide, 30 ml of methyl acetate, and 32 ml of acetic acid. The mixture was reacted in the same manner as in Example 1. The total pressure was 40 kg/cm$^2$G, which was the sum of a partial pressure of CO of 35 kg/cm$^2$G, and a partial pressure of H$_2$ of 5 kg/cm$^2$. The reaction conditions included heating the mixture to 175° C. and reacting it at this temperature 1 hour.

EXAMPLE 17 (Comparative)

This example was carried out in the same manner as in Example 16, except that no N-methylpyrrolidone was added.

A white solid precipitate was formed in the concentrated solution.

EXAMPLE 18

This example was carried out in the same manner as in Example 16, except that 30 ml of acetic anhydride was used instead of acetic acid.

EXAMPLE 19 (Comparative)

This example was carried out in the same manner as in Example 18, except that no N-methylpyrrolidone was added.

EXAMPLE 20

This example was carried out in the same manner as in Example 18, except that 22 mmol of N,N-dimethylacetamide was used instead of N-methylpyrrolidone.

TABLE 2

| Example | Acetic acid (ml) | Acetic anhydride (ml) | Metaboric acid (mmol) | Rate of reaction (mol/l. hr) | Conversion of methyl acetate (%) | Yield of acetic anhydride (%) | Solid precipitate in concentrated solution |
|---|---|---|---|---|---|---|---|
| 6 | 23 | 8 | 23 | 6.3 | 92.8 | 75.1 | nil |
| 7 (comp.) | 24 | 8 | 0 | 4.7 | 84.8 | 74.0 | white |
| 8 | 15 | 16 | 23 | 5.3 | 76.0 | 69.7 | nil |
| 9 (comp.) | 16 | 16 | 0 | 3.9 | 63.6 | 62.8 | white |
| 10 | 7 | 24 | 23 | 5.2 | 59.9 | 59.9 | nil |
| 11 (comp.) | 8 | 24 | 0 | 2.7 | 58.4 | 53.0 | white |

EXAMPLE 21

This example was carried out in the same manner as in Example 18, except that 11 mmol of chromium acetate was used instead of aluminum acetate.

EXAMPLE 22 (Comparative)

This example was carried out in the same manner as in Example 21, except that no N-methylpyrrolidone was added. A green solid (chromium acetate) was formed in the reaction mixture.

What is claimed is:

1. A carbonylation process for preparing an oxyacetyl compound, which comprises: reacting carbon monoxide with an oxy-methyl material selected from the group consisting of methyl carboxylates, dimethyl ether and mixtures thereof with methanol, in the presence of a rhodium catalyst, an iodine compound, a metallic accelerator in which the metal is selected from the group consisting of aluminum, chromium and titanium, and in the presence of a boron compound, the atomic ratio of boron relative to the metal of the metallic accelerator being in the range of from 0.1-15.0 to 1.

2. A process as claimed in claim 1, wherein the atomic ratio of metal of said metal accelerator to the amount of rhodium in the rhodium catalyst is in the range of from 0.1-100.0 to 1.

3. A process as claimed in claim 1, wherein the metallic accelerator is present in a concentration of at least 0.1 mole per liter.

4. In a process for the preparation of an oxy-acetyl compound by carbonylation of an oxy-methyl material selected from the group consisting of methyl carboxylates, dimethyl ether and mixtures thereof with methanol, which comprises: at a temperature in the range of from 130° to 250° C., reacting (a) carbon monoxide gas having a partial pressure of from 1 to 100 kg/cm$^2$G, with (b) said oxy-methyl material, which material is dissolved in an anhydrous reaction liquid containing a catalytically effective amount of a catalyst system consisting essentially of (i) a rhodium carbonylation catalyst, (ii) an iodine compound and (iii) an effective amount of a metallic accelerator selected from the group consisting of aluminum, chromium, titanium and compounds thereof, said metallic accelerator being effective to accelerate the transformation of said oxy-methyl material to said oxy-acetyl compound, the improvement which comprises: said reaction liquid also containing a boron compound selected from the group consisting of metaboric acid, boron hydride, sodium borohydride, boric acid, borate esters and boron acetate, the atomic ratio of boron to the metal of said metallic accelerator being in the range of from 0.1/1 to 15/1, said boron compound being effective to solubilize said metallic accelerator in the reaction liquid.

5. The process as claimed in claim 4 in which said atomic ratio is from 0.4/1 to 2/1.

6. The process as claimed in claim 4 in which said boron compound is metaboric acid.

7. A carbonylation process for preparing an oxyacetyl compound, which comprises: reacting carbon monoxide with an oxy-methyl material selected from the group consisting of methyl carboxylates, dimethyl ether and mixtures thereof with methanol, in the presence of a rhodium catalyst, an iodine compound, a metallic accelerator in which the metal is selected from the group consisting of aluminum, chromium and titanium, and in the presence of a bismuth compound, the atomic ratio of bismuth relative to the metal of the metallic accelerator being in the range of from 0.05-2.0 to 1.

8. A process as claimed in claim 7, wherein the atomic ratio of metal of said metal accelerator to the amount of rhodium in the rhodium catalyst is in the range of from 0.1-100.0 to 1.

9. A process as claimed in claim 7, wherein the metallic accelerator is present in a concentration of at least 0.1 mole per liter.

10. In a process for the preparation of an oxy-acetyl compound by carbonylation of an oxy-methyl material selected from the group consisting of methyl carboxylates, dimethyl ether and mixtures thereof with methanol, which comprises: at a temperature in the range of from 130° to 250° C., reacting
(a) carbon monoxide gas having a partial pressure of from 1 to 100 kg/cm$^2$G, with
(b) said oxy-methyl material, which material is dissolved in an anhydrous reaction liquid containing a catalytically effective amount of a catalyst system consisting essentially of (i) a rhodium carbonylation catalyst, (ii) an iodine compound and (iii) an effective amount of a metallic accelerator selected from the group consisting of aluminum, chromium, titanium and compounds thereof, said metallic accelerator being effective to accelerate the transformation of said oxy-methyl material to said oxy-acetyl compound, the improvement which comprises: said reaction liquid also containing a bismuth compound selected from the group consisting of bismuth nitrate and bismuth acetate, the atomic ratio of bismuth to the metal of said metallic accelerator being in the range of from 0.05/1 to 2/1, said bismuth compond being effective to solubilize said metallic accelerator in the reaction liquid.

11. The process as claimed in claim 10 in which said atomic ratio is from 0.1/1 to 1/1.

12. The process as claimed in claim 10 in which said bismuth compound is bismuth nitrate.

* * * * *